United States Patent
Snyder

(10) Patent No.: US 9,483,622 B1
(45) Date of Patent: Nov. 1, 2016

(54) PAIN VISUALIZATION SYSTEM AND METHOD

(75) Inventor: Seth Snyder, Providence, RI (US)

(73) Assignee: HUMANA INC., Louisville, KY (US)

( * ) Notice: Subject to any disclaimer, the term of this patent is extended or adjusted under 35 U.S.C. 154(b) by 129 days.

(21) Appl. No.: 13/004,603

(22) Filed: Jan. 11, 2011

Related U.S. Application Data

(60) Provisional application No. 61/293,878, filed on Jan. 11, 2010.

(51) Int. Cl.
| | | |
|---|---|---|
| *G06F 19/00* | (2011.01) | |
| *A61B 5/00* | (2006.01) | |
| *G06F 3/0481* | (2013.01) | |
| *G06Q 50/00* | (2012.01) | |

(52) U.S. Cl.
CPC ......... *G06F 19/3487* (2013.01); *A61B 5/4824* (2013.01); *A61B 5/7435* (2013.01); *G06F 3/0481* (2013.01); *G06Q 50/01* (2013.01)

(58) Field of Classification Search
None
See application file for complete search history.

(56) References Cited

U.S. PATENT DOCUMENTS

| | | | | |
|---|---|---|---|---|
| 6,529,195 B1* | 3/2003 | Eberlein | | 345/441 |
| 7,374,536 B1* | 5/2008 | Taylor | | 600/300 |
| 8,046,241 B1* | 10/2011 | Dodson | | 705/2 |
| 2002/0052763 A1* | 5/2002 | Jung Richardson | | 705/3 |
| 2003/0139652 A1* | 7/2003 | Kang et al. | | 600/300 |
| 2004/0078215 A1* | 4/2004 | Dahlin et al. | | 705/2 |
| 2005/0192972 A1* | 9/2005 | Daignault, Jr. | | 707/100 |
| 2007/0055481 A1* | 3/2007 | Baird et al. | | 702/183 |
| 2008/0177570 A1* | 7/2008 | Craine | | 705/2 |
| 2008/0297527 A1* | 12/2008 | Daignault, Jr. | | 345/581 |
| 2009/0005649 A1* | 1/2009 | Baird et al. | | 600/300 |
| 2009/0125333 A1* | 5/2009 | Heywood et al. | | 705/3 |
| 2010/0070306 A1* | 3/2010 | Dvorak et al. | | 705/3 |
| 2011/0118554 A1* | 5/2011 | Stakutis et al. | | 600/300 |

* cited by examiner

*Primary Examiner* — William Thomson
*Assistant Examiner* — Davin Sands
(74) *Attorney, Agent, or Firm* — Standley Law Group LLP

(57) ABSTRACT

A computerized pain visualization system and method. A web-based application and interface allows individuals to anonymously share information about where they hurt or specific regions of the body that are most worrisome to them. The web-based application comprises a visual interface that supports selection of parts or regions on an image of a human body. The data becomes viewable and filterable by geographic location, age, sex, or a variety of other data sets collected from the anonymous users. In an example embodiment, Users register and sign in at a web site. A selectable body interface is presented and the user is prompted to select one or more pain locations on the virtual body. The user's selections are recorded in a database. Another page of the application presents a search option that facilitates searching and visualizing the data, filterable by users' registration information.

13 Claims, 10 Drawing Sheets

PAIN VISUALIZATION SYSTEM AND METHOD

CROSS-REFERENCE TO RELATED APPLICATION

This application claims priority to U.S. Provisional Patent Application Ser. No. 61/293,878, filed Jan. 11, 2010, titled Pain Visualization System and Method, the content of which is incorporated herein by reference.

BACKGROUND

People today use social networking services to share information about themselves and in many instances, to connect with others who share similar experiences or feelings. Many people are willing to share detailed or intimate information about theft own health in order to connect with others who may have similar problems or conditions. Although people are willing to discuss health issues and to provide information about theft own health problems or conditions, it is often difficult for them to qualify and/or quantify various health conditions and to communicate them to others in a meaningful way. Social networking services generally facilitate communication between groups of individuals, but they do not have features or functionality that specifically support communication regarding health problems or conditions. There is a need for a system and method that uses social networking features and functionality and that facilitates communication of health information, problems, and conditions.

SUMMARY

The present disclosure describes a web-based application and interface for individuals to anonymously share information about where they hurt or the specific regions of the body that are most worrisome to them. The web-based application comprises a highly visual interface that supports selection of parts or regions on an image of a virtual human body. The data becomes viewable and filterable by geographic location, age, sex, or a variety of other data sets collected from the anonymous users. It is a visualization tool that provides a powerful way for individuals to communicate health concerns without intruding into their privacy. The data may be analyzed to present visualizations of pains and worries over time, geography, etc.

In an example embodiment, users register and sign in at a web site. A selectable body interface is presented and the user is prompted to select one or more pain locations on the virtual body. The user's selections are recorded in a database. Another page of the application presents a search option that facilitates searching and visualizing the data, filterable by users' registration information.

DETAILED DESCRIPTION

Figure 1:
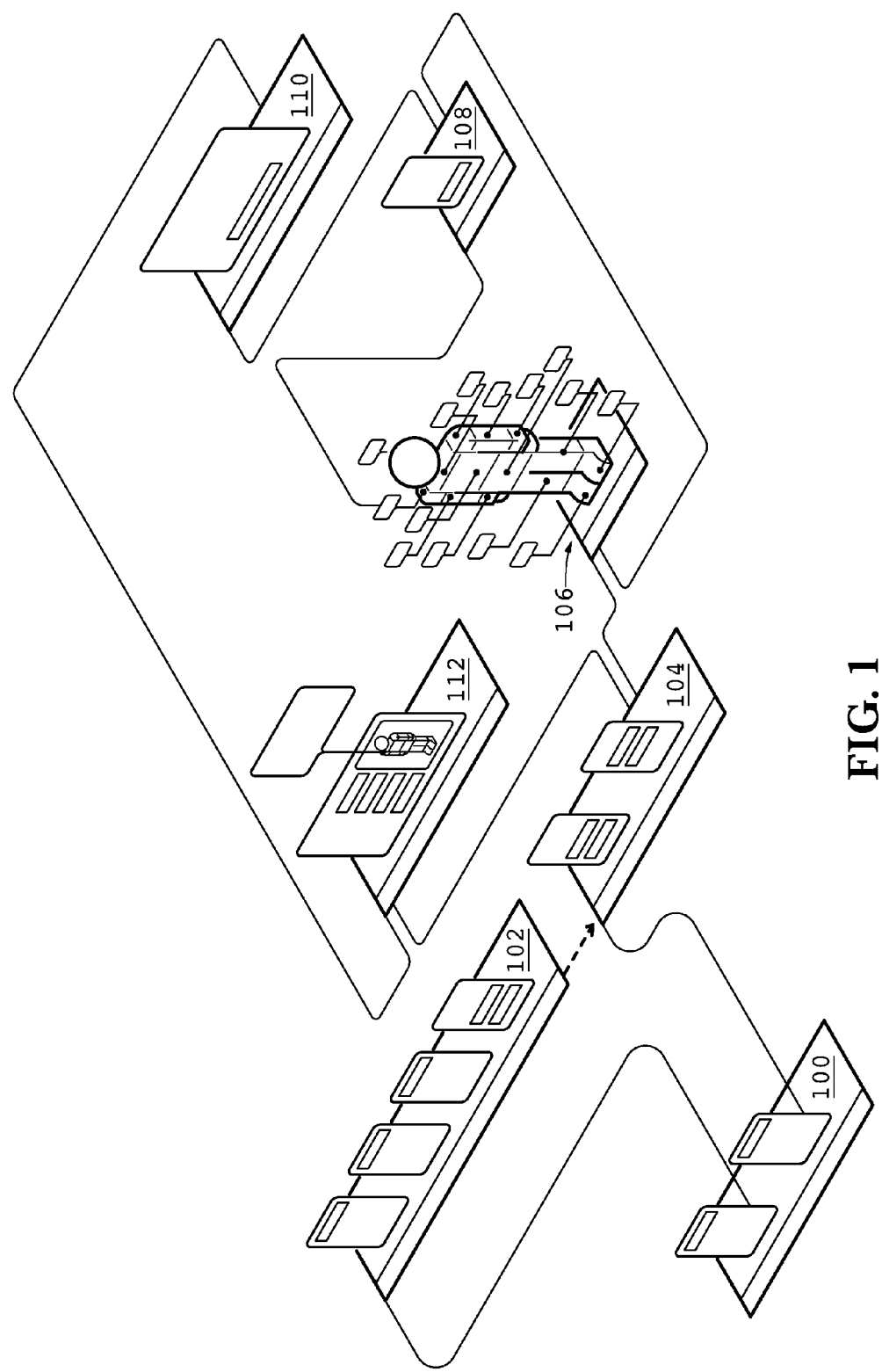
FIG. 1 is a flow diagram of a virtual pain visualization system according to an example embodiment.

Referring to FIG. 1, a flow diagram of a virtual pain visualization system according to an example embodiment is shown. Initially, a user registers with the system 100. In a registration process 102, a user may be prompted to provide location information, an age, a sex, and a username and password. Registered users may sign in 100 by entering the username and password provided during the registration process.

After signing in, a user may select a "pain selection" or a "pain search" option 104. If a user selects the "pain selection" option, a web page with a virtual body is displayed 106. The body may be visually divided into areas or regions such as "right foot," "left foot," "right leg," "left leg," "stomach," "chest," etc. The body may be rotated to allow the user to access front and back areas or regions. The user is prompted to identify one or more areas or regions in which he or she is experiencing pain. After selecting an area or region (e.g., by clicking on it), the user may be prompted to confirm the selection 108. The selected area and date is registered in a database and a confirmation message (e.g., "anonymous user's pain in right shoulder registered on Nov. 20, 2009") is displayed to the user 110.

If a user selects the "pain search" option, a web page with search criteria and a virtual body is presented 112. The user may be prompted to select, for example, a location, age, sex, and/or date. Upon submission of the search criteria, the database is searched and the web page is refreshed to identify areas or regions of the virtual body relevant to the user's search criteria. The web page may further display a message that lists the number of "pains" recorded by users that match the selection criteria. For instance, a user may search for pain data entered the day before, pain data entered yesterday by women, or pain data entered yesterday for women who are 30-40 years old.

Figure 2:
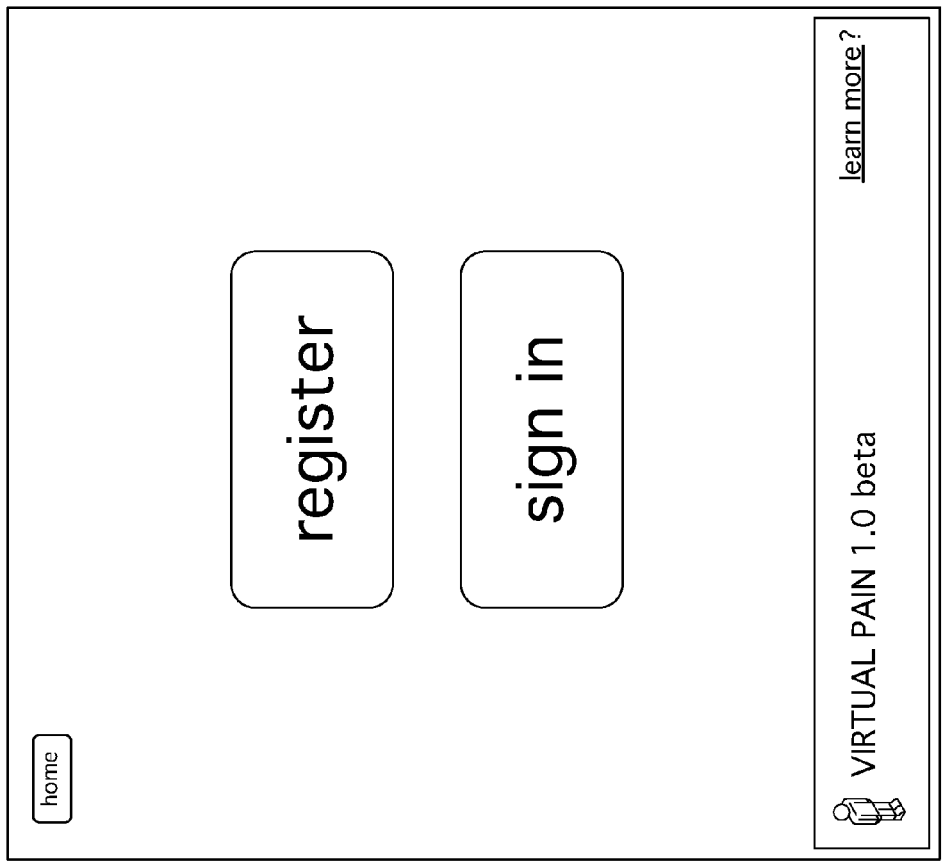
FIGS. 2-7 are sample screens for a web-based application according to an example embodiment.
Figure 3:
Figure 4:
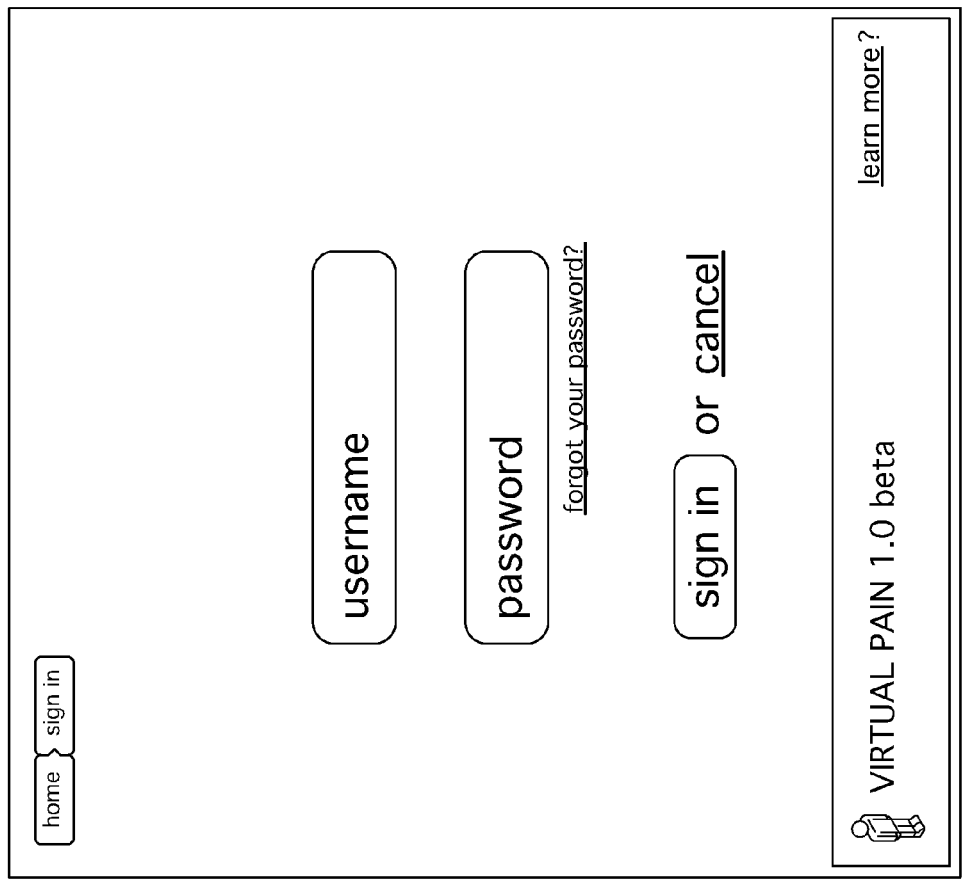
Figure 5:
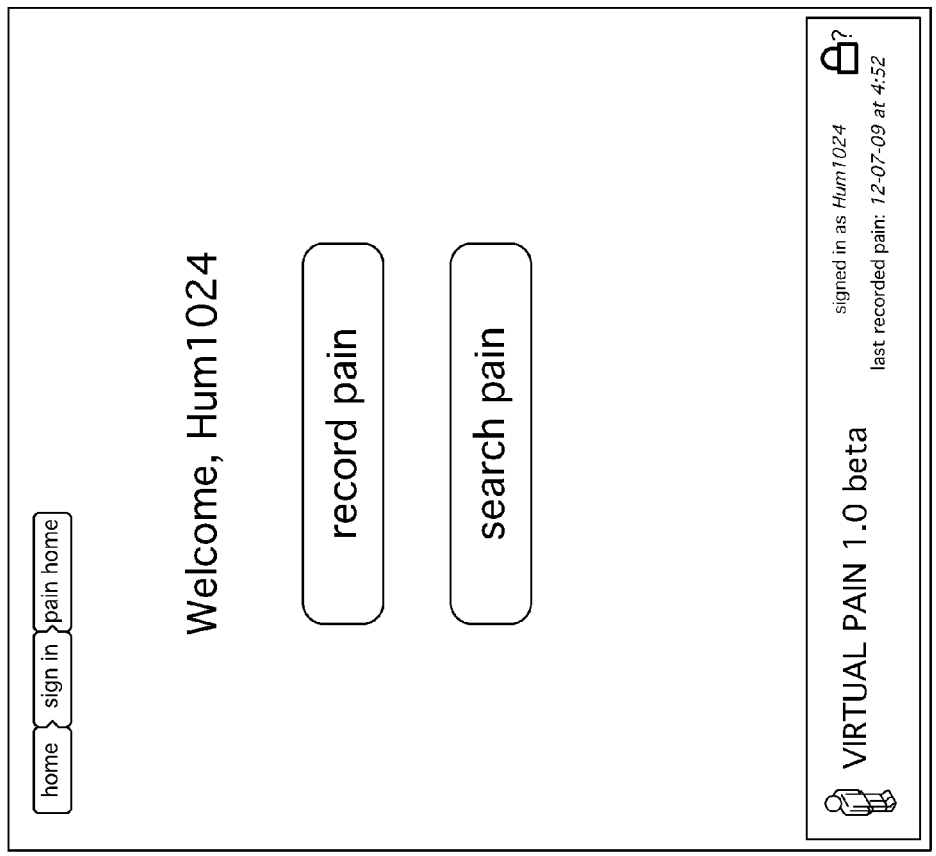

Referring to FIG. 2, a sample "register/sign in" page according to an example embodiment is shown. Referring to FIG. 3, a sample "register" page according to an example embodiment is shown. A first time user may be prompted to enter a username and password and further provide location, age, and sex data. Referring to FIG. 4, a sample "sign in" page according to an example embodiment is shown. Referring to FIG. 5, a "welcome" page according to an example embodiment is shown. In an example embodiment, the user is prompted to select a "record pain" option or a "search pain" option.

Figure 6A:
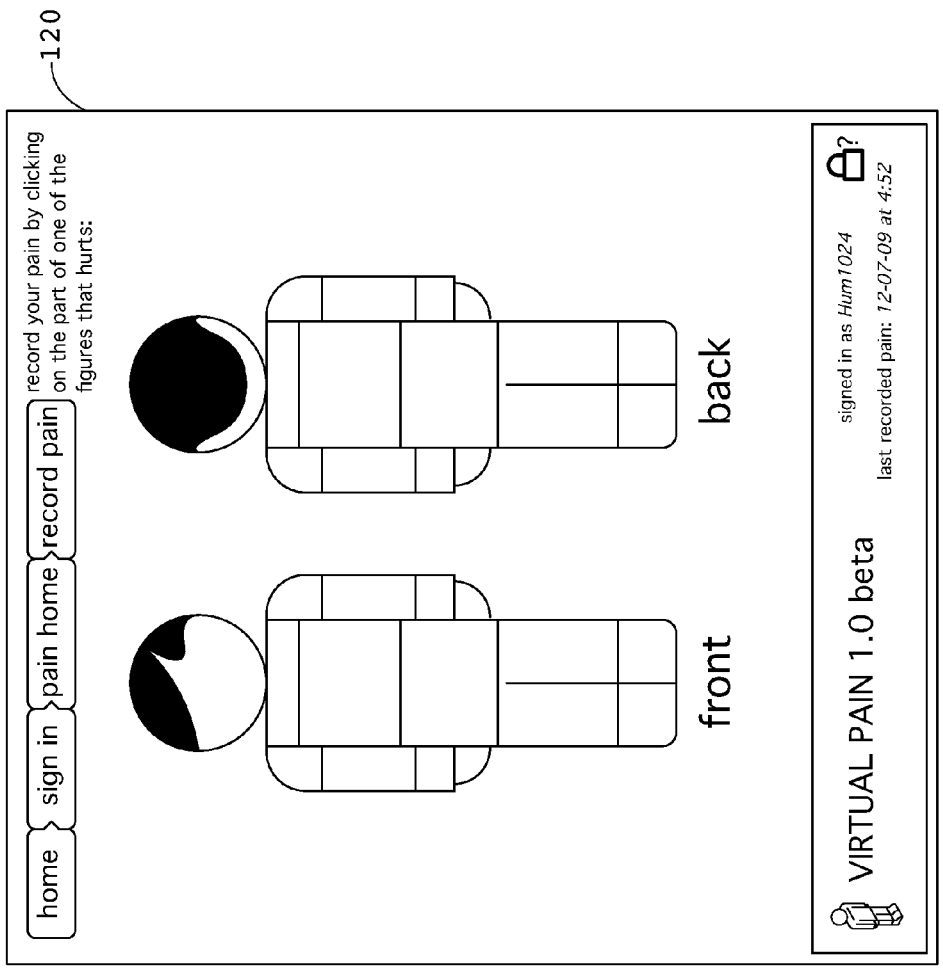
Figure 6B:
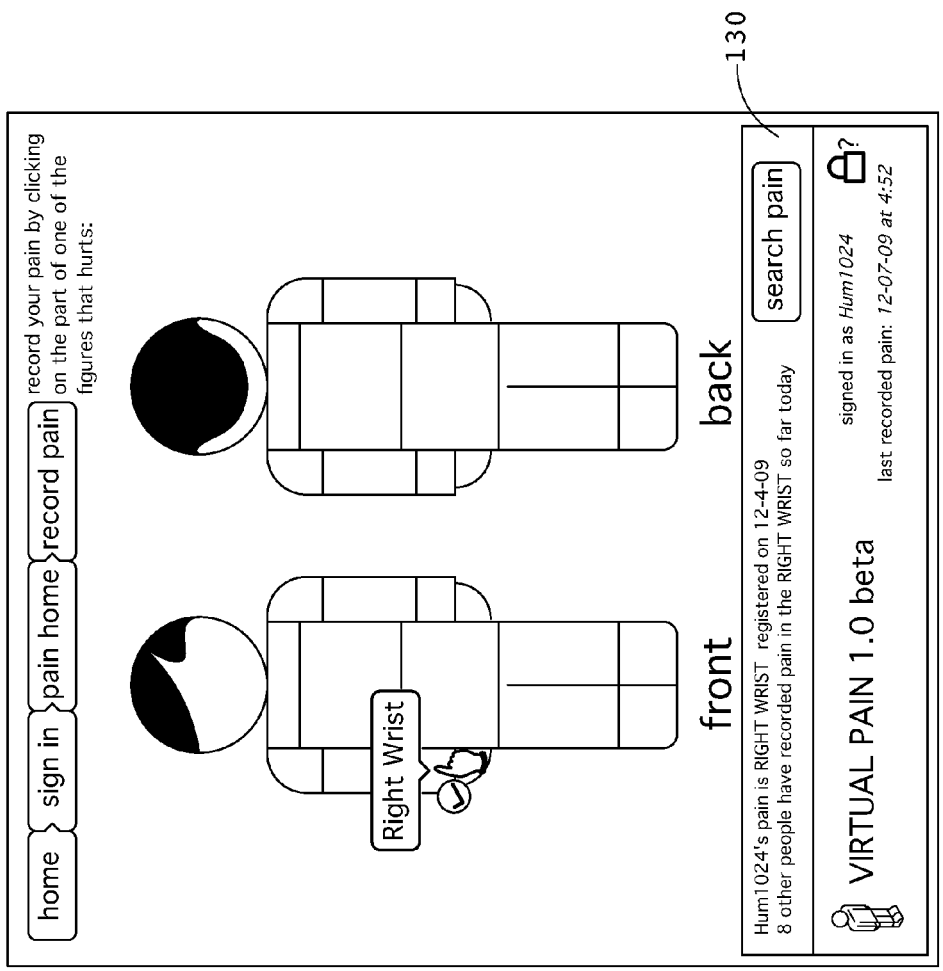
Figure 6C:
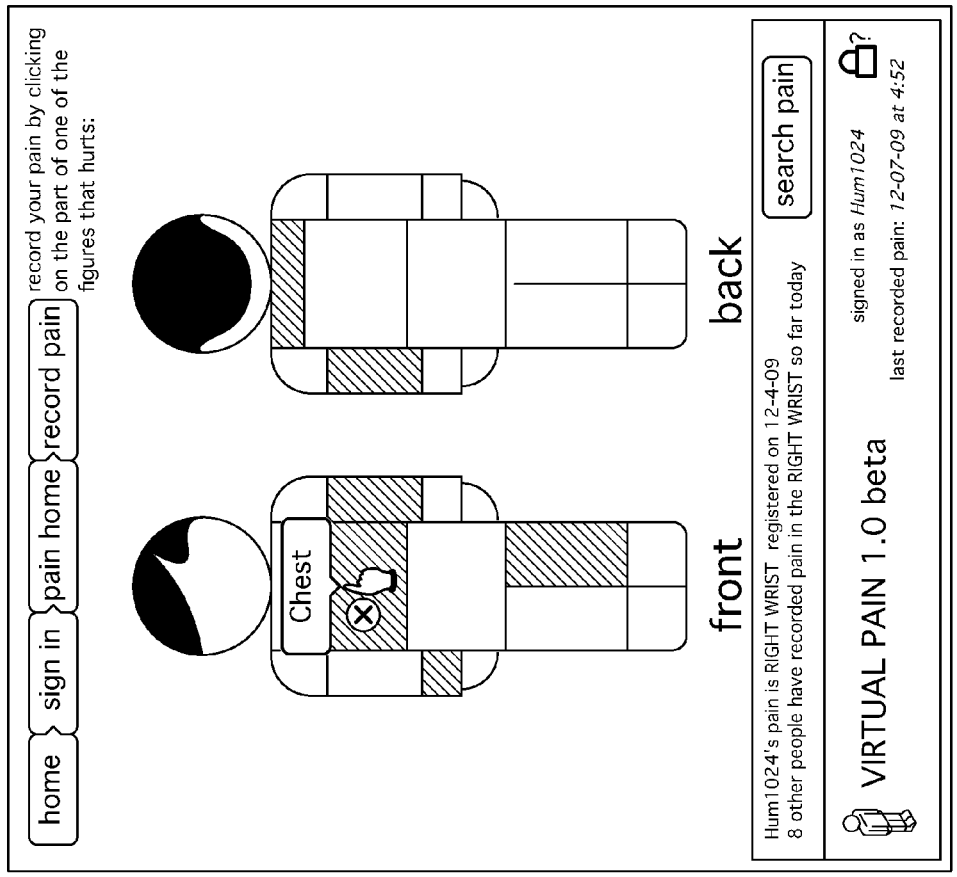

Referring to FIGS. 6A-6C, sample "record pain" pages according to an example embodiment are shown. Referring to FIG. 6A, initially, a virtual body or human figure is presented on the display page with lines to demarcate areas, regions, or parts. The virtual body may comprise a front and back to allow the user to more clearly identify the area of pain he or she is experiencing. The page further comprises a message area 120 with instructions to the user (e.g., "record your pain by clicking on the part of one of the figures that hurts").

Referring to FIG. 6B, when the user selects an area, region, or part of the virtual body, the display page is refreshed to identify the selected area, region, or part (e.g., "right wrist"). The selection is then registered in a database. In an example embodiment, the selection is registered with user's non-identifying data (e.g., location, age, and sex) and the date. The user may then select the "search pain" option to learn about others that have the same pain. Referring to FIG. 6C, a user that has selected an incorrect area, region, or part can "undo" a selection by selecting the area, region, or part a second time. The second selection unregisters the previously selected area, region, or part.

Figure 7A:
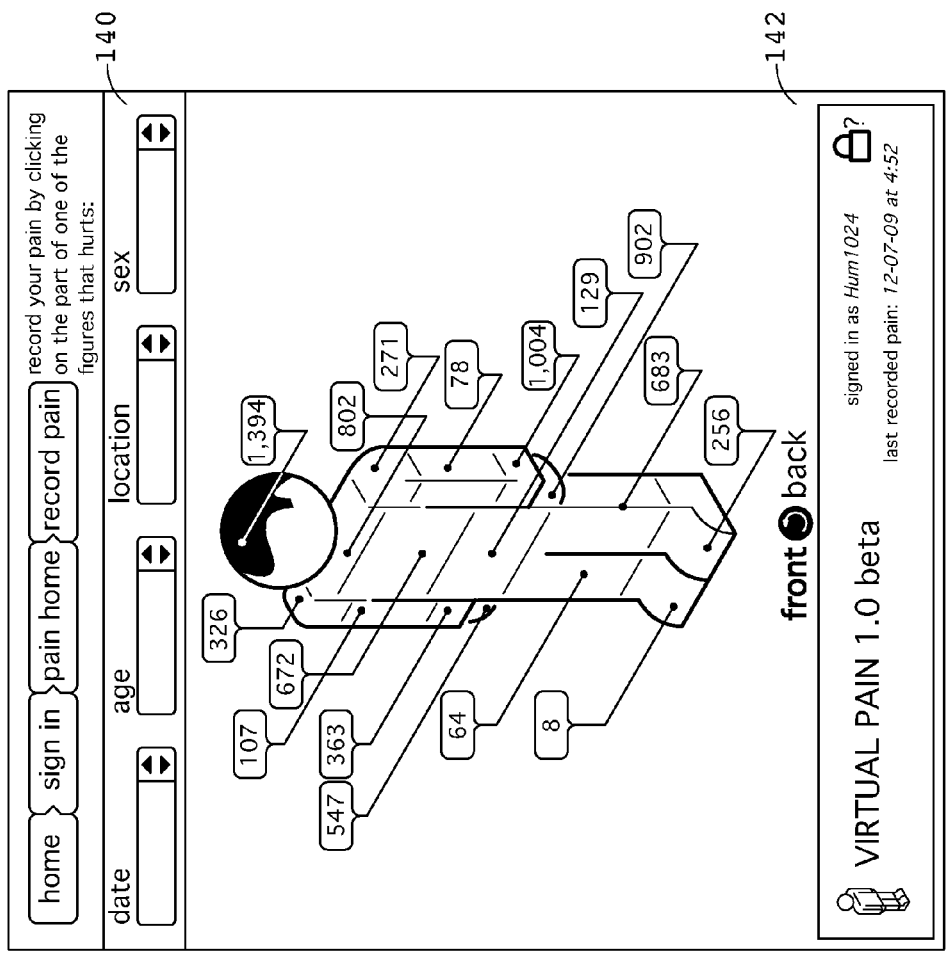
Figure 7B:
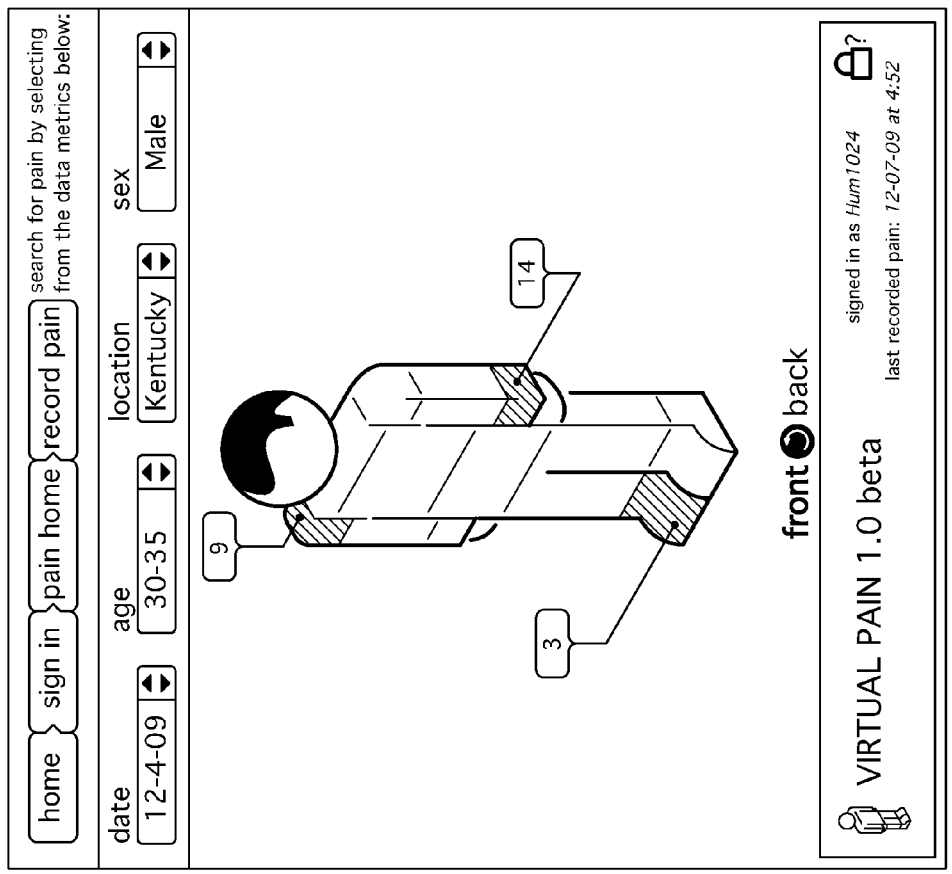

Referring to FIGS. 7A and 7B, a "search pain" page according to an example embodiment is shown. Referring to FIG. 7A, the "search pain" page may initially indicate for each area, region, or part the number of users that have registered pain in that area/region/part 142. The page further comprises a section for entering search criteria 140 to filter the results. In an example embodiment, the user may enter selection criteria for date, age, location, and sex. Referring to FIG. 7B, a search results display page identifies on the virtual body the areas, regions, or parts that match the search criteria as well as the related number of users.

A computerized virtual pain interface system and method is described in reference to the appended figures. The description with reference to figures is made to exemplify the disclosed computerized system and method and is not intended to limit the system and method to the representations in the figures. From the foregoing description, it can be understood that there are various ways to display a virtual body and illustrate selected areas or regions of pain while still falling within the scope of the present invention. In addition, the type of data that is registered and available for searching may be varied while still falling within the scope of the present invention. As such, while certain embodiments of the present invention are described in detail above, the scope of the invention is not to be considered limited by such disclosure, and modifications are possible without departing from the spirit of the invention as evidenced by the following claims.

What is claimed is:

1. A computerized pain visualization method comprising:
   (a) receiving at a server user registration data for a plurality of users;
   (b) receiving at said server from each of said plurality of users a first selection of a record pain option;
   (c) in response to receiving said first selection of said record pain option, generating at said server for display at user computers of said plurality of users a body image;
   (d) visually dividing said body image into a plurality of user selectable body areas;
   (e) receiving at said server from each of said plurality of users a second selection of at least one selectable body area;
   (f) storing in a database at said server for each of said plurality of users non-identifying user data and body identifying data for said second selection of at least one selectable body area, the non-identifying user data including geographic location, age, sex, and date corresponding to when said second selection is received;
   (g) receiving at said server from one of said plurality of users a third selection of said record pain option;
   (h) receiving at said server from said one of said plurality of users a fourth selection of said at least one selectable body area and registering said fourth selection of said at least one selectable body area in the database along with the geographic location, age, and sex of said one of said plurality of users and a date corresponding to when said fourth selection is received;
   (i) searching said database to:
      (i) calculate a number of said plurality of users that recorded pain for said at least one selectable one body area on said date corresponding to when said fourth selection is received; and
      (ii) determine a last recordation date for said one of said plurality of users recordation of pain;
   (j) generating at said server an updated body image for display at said user computer of said one of said plurality of users to identify on said body image:
      (i) a registration date for said one of said plurality of users recordation of pain for said at least one selectable body area; and
      (ii) said number of said plurality of users that recorded pain for said at least one selectable body area on said date corresponding to when said fourth selection is received;
   (k) receiving at said server a selection of a search pain option from another one of said plurality of users;
   (l) receiving at said server inputted search criteria from said another one of said plurality of users including date, age, geographic location, and sex;
   (m) searching said database for body identifying data matching said inputted search criteria;
   (n) generating at said server for display at a user computer of said another one of said plurality of users an updated view of said body image to identify on said body image:
      (i) at least one body area consistent with said body identifying data matching said inputted search criteria; and
      (ii) a number of said plurality of users that recorded pain for said at least one body area matching said inputted search criteria.

2. The computerized pain visualization method of claim 1 wherein generating at a server for display at said user computer a body image comprises generating a full human figure.

3. The computerized pain visualization method of claim 2 wherein identifying on said body image a plurality of user selectable body areas comprises identifying a head area, a chest area, two arm areas, and two leg areas.

4. The computerized pain visualization method of claim 2 wherein identifying on said body image a plurality of user selectable body areas comprises identifying a head area, a neck area, a chest area, a stomach area, two upper arm areas, two middle arm areas, two lower arm areas, two wrist areas, two upper leg areas, and two lower leg areas.

5. The computerized pain visualization method of claim 2 wherein generating a full human figure comprises generating a first figure representative of a front of a human and a second figure representative of a back of a human.

6. The computerized pain visualization method of claim 1 wherein generating at a server for display at a user computer at a body image comprises generating a partial human figure.

7. The computerized pain visualization method of claim 1 wherein said non-identifying user data is selected from the group consisting of location, age, and sex.

8. A computerized pain visualization system comprising a server with programming instructions to:
   (a) receive at said server user registration data for a plurality of users;
   (b) receive at said server from each of said plurality of users a first selection of a record pain option;
   (c) in response to receiving said first selection of said record pain option, generate at said server for display at user computers of said plurality of users a body image;
   (d) visually divide said body image into a plurality of user selectable body areas;
   (e) receive at said server from each of said plurality of users a second selection of at least one selectable body area;
   (f) store in a database for each of said plurality of users non-identifying user data and body identifying data for said second selection of at least one selectable body area, the non-identifying user data including geographic location, age, sex, and date corresponding to when said second selection is received;

(g) receive at said server from one of said plurality of users a third selection of said record pain option;

(h) receive at said server from said one of said plurality of users a fourth selection of said at least one selectable body area;

(i) search said database to:
  (i) calculate a number of said plurality of users that recorded pain for said at least one selectable area on said date corresponding to when said fourth selection is received; and
  (ii) determine a last recordation date for said one of said plurality of users recordation of pain;

(j) generate at said server an updated body image for display at said user computer of said one of said plurality of users with:
  (i) a registration date for said one of said plurality of users recordation of pain for said at least one selectable body area; and
  (ii) said number of said plurality of users that recorded pain for said at least one body area on said date corresponding to when said fourth selection is received;

(k) receiving at said server a selection of a search pain option from another one of said plurality of users;

(l) receiving at said server inputted search criteria from said another one of said plurality of users including date, age, geographic location, and sex;

(m) searching said database for body identifying data matching said inputted search criteria;

(n) generating at said server for display at a user computer of said another one of said plurality of users an updated view of said body image to identify on said body image:
  (i) at least one body area consistent with said body identifying data matching said inputted search criteria; and
  (ii) a number of said plurality of users that recorded pain for said at least one body area matching said inputted search criteria.

9. The computerized pain visualization system of claim 8 wherein said body image comprises a full human figure.

10. The computerized pain visualization system of claim 8 wherein said plurality of user selectable body areas comprises a head area, a chest area, two arm areas, and two leg areas.

11. The computerized pain visualization system of claim 8 wherein said plurality of user selectable body areas comprises a head area, a neck area, a chest area, a stomach area, two upper arm areas, two middle arm areas, two lower arm areas, two wrist areas, two upper leg areas, and two lower leg areas.

12. The computerized pain visualization system of claim 9 wherein said full human figure comprises a first figure representative of a front of a human and a second figure representative of a back of a human.

13. The computerized pain visualization system of claim 8 wherein said body image comprises a partial human figure.

* * * * *